United States Patent
Kirby

(10) Patent No.: US 10,532,200 B2
(45) Date of Patent: Jan. 14, 2020

(54) MICROPENETRATOR DEVICE FOR PENETRATING A BIOLOGICAL BARRIER

(71) Applicant: Xobaderm Limited, Cardiff South Glamorgan (GB)

(72) Inventor: Andrew James Kirby, Cardiff South Glamorgan (GB)

(73) Assignee: Xobaderm Limited, Cardiff South Glamorgan (GB)

( * ) Notice: Subject to any disclaimer, the term of this patent is extended or adjusted under 35 U.S.C. 154(b) by 85 days.

(21) Appl. No.: 15/528,821

(22) PCT Filed: Nov. 25, 2015

(86) PCT No.: PCT/GB2015/053592
§ 371 (c)(1),
(2) Date: May 23, 2017

(87) PCT Pub. No.: WO2016/083803
PCT Pub. Date: Jun. 2, 2016

(65) Prior Publication Data
US 2017/0319839 A1    Nov. 9, 2017

(30) Foreign Application Priority Data

Nov. 25, 2014  (GB) .................................. 1420946.4
Oct. 8, 2015  (GB) .................................. 1517832.0

(51) Int. Cl.
*A61M 37/00*  (2006.01)
*A61B 17/20*  (2006.01)
*A61B 17/00*  (2006.01)

(52) U.S. Cl.
CPC ....... *A61M 37/0015* (2013.01); *A61B 17/205* (2013.01); *A61B 2017/00747* (2013.01);
(Continued)

(58) Field of Classification Search
CPC ........ A61M 37/0015; A61M 2037/003; A61M 2037/0046; A61M 2037/0023; A61M 2037/0053; A61B 17/205
See application file for complete search history.

(56) References Cited

U.S. PATENT DOCUMENTS 4,966,159 A     10/1990  Maganias
2003/0220656 A1  11/2003  Gartstein et al.
(Continued)

FOREIGN PATENT DOCUMENTS

CN   103203072 A    7/2013
JP   2014097163 A *  5/2014 ........ A61M 37/0015
(Continued)

*Primary Examiner* — Emily L Schmidt
(74) *Attorney, Agent, or Firm* — Dinsmore & Shohl LLP

(57) ABSTRACT

A device that may be placed on a biological barrier can be used to perforate the biological barrier for a variety of purposes such as cosmetic, scar treatment or for the delivery of active agents. A flexible substrate has a first side and a second opposing side and a plurality of micro-penetrator arrangements each comprising a head and a first and second projection, for penetrating a biological barrier, extending from the head. The first and second projection at least partially extend through the flexible substrate towards the first side. The head comprises an elongate arm for spacing apart the first and second projections. A force is applied to the second side causing flexing of the flexible substrate and pushing the projections into communication with a biological barrier.

15 Claims, 11 Drawing Sheets

(52) U.S. Cl.
CPC .......... *A61M 2037/003* (2013.01); *A61M 2037/0023* (2013.01); *A61M 2037/0046* (2013.01); *A61M 2037/0053* (2013.01)

(56) References Cited

U.S. PATENT DOCUMENTS

| | | | | |
|---|---|---|---|---|
| 2007/0078414 | A1* | 4/2007 | McAllister | A61B 17/205 604/272 |
| 2007/0270738 | A1* | 11/2007 | Wu | A61B 17/205 604/46 |
| 2007/0293816 | A1* | 12/2007 | Chan | A61M 37/0015 604/46 |
| 2010/0305473 | A1 | 12/2010 | Yuzhakov | |
| 2013/0144257 | A1* | 6/2013 | Ross | A61M 37/0015 604/506 |
| 2014/0031897 | A1 | 1/2014 | Liebl | |

FOREIGN PATENT DOCUMENTS

| | | | |
|---|---|---|---|
| WO | 0108717 | A1 | 2/2001 |
| WO | 2010140760 | A2 | 12/2010 |
| WO | 2014126317 | A1 | 8/2014 |

* cited by examiner

FIG. 11
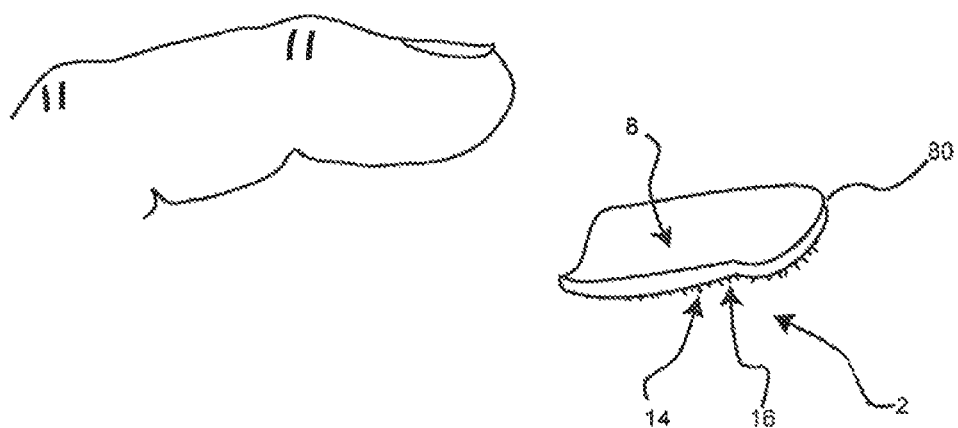
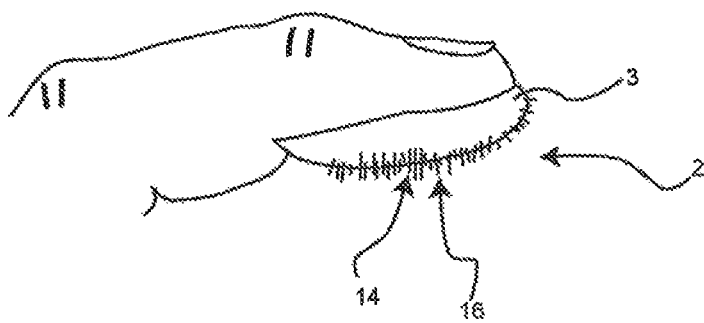

MICROPENETRATOR DEVICE FOR PENETRATING A BIOLOGICAL BARRIER

CROSS REFERENCE TO RELATED APPLICATIONS

This application claims priority to PCT/GB2015/053592 filed Nov. 25, 2015 which claims priority to GB1420946.4 filed Nov. 25, 2014 and GB1517832.0 filed Oct. 8, 2015. The entirety of each is incorporated herein.

The present invention relates to a device that may be placed on a biological barrier, such as the stratum corneum, and then be used to perforate the biological barrier for a variety of purposes such as cosmetic, scar treatment or for the delivery of active agents for systemic or local treatment or vaccination.

Microneedles have been an interesting research topic for many years in the field of transdermal drug delivery and also in aesthetic dermatology. It has been in this aesthetic field where the first microneedle products have appeared. Treatment using devices such as a barrel having microneedles extending from the barrel which is rolled over the skin are now being offered in salons and clinics all over the world, and have found use in treatment of scars, stretch marks and wrinkles. Microneedling has various advantages over laser and other aesthetic treatments, not least being that microneedle devices are much less expensive. Microneedles have been used in research for transdermal delivery of drugs and vaccines, but there have been limitations due to complexity of manufacture and scale up, as well as the "bed of nails" effect creating difficulty in attaining reliable and reproducible penetration. Also the manufacturing method creates structures that are inherently difficult to integrate with existing patch and other formulations. There exists a need to create a low cost, simple to manufacture, microneedle device that can be integrated with existing scar treatments or transdermal drug treatments, that can reliably produce penetration over the entire array or needles. A partial answer to these problems was described in patent no WO 2006/018642 by the present inventor. In that patent, a flexibly backed microneedle system was made by printing high aspect ratio structures by building up layers of curable material like adhesives. This would allow a microneedle device where the needle material was different to the backing material, and the flexibility of the backing membrane would allow each needle to be individually pushed from behind to reduce the bed of nails effect. There are several inherent problems with this technique, however, including the extreme difficulty of getting sharp enough tips that simultaneously are strong enough to withstand shear forces so as not to break in the skin. Also the flexibility of the membrane that the "needles" were deposited on leads to needles that will fall over to one side instead of penetrating the biological barrier.

The present invention overcomes the problems with the previous methodologies, providing a low-cost, minimally invasive device for treatment of a biological material such as skin and additionally that is capable of the delivery of pharmaceutical, cosmetic or immunological activities or other substances through a biological barrier. The barrier may be the stratum corneum, allowing a low pain, low skill alternative to conventional needles, with greater reproducibility than solid backed microneedles. For aesthetic and wound healing treatment, the biological barrier may be the epidermis or dermis. The skin may not be intact such as in the case of a wound, and may be thickened in the case of a scar or psoriasis or other lesion.

According to a first aspect of the present invention there is a device for penetration of a biological barrier, the device comprising a flexible substrate having a first side and a second opposing side, the device further comprising a plurality of micropenetrator arrangements each comprising a head and a first and second projection for penetrating a biological barrier extending from the head, wherein the first and second projection at least partially extend through the flexible substrate towards the first side, wherein the head comprises an elongate arm spacing apart the first and second projections In an alternative definition there is a device for penetration of a biological barrier, the device comprising a flexible substrate having a first side forming a biological barrier contact surface and a second opposing side, the device further comprising a plurality of micropenetrator arrangements each comprising a head and a first and second projection for penetrating a biological barrier extending from the head, wherein the first and second projection at least partially extend through the flexible substrate towards the first side.

Upon application of a force to the second side of the substrate the plurality of projections project into a biological barrier. In use therefore the projections of one or more of the micropenetrator arrangements project from the first side and into the biological barrier.

The ability of the micropenetrator arrangements to have independence of movement, even if limited, is preferable in order to overcome the "bed of nails" effect. This results in localising of the force applied, thereby making penetration significantly easier. It is therefore important that the substrate is flexible. In use therefore the substrate may conform to the anatomical geometry of the biological barrier. It is preferable but not essential that the first side is a biological barrier contact surface. The substrate preferably also conforms to be anatomically geometry of an application, which is beneficially a user's finder giving increased control of application.

The ability to activate only part of the device, i.e. activate one or more solid micropenetrators will limit effect upon others, means that treatment or dosage (in the event of the device being used to deliver a drug for example) can be controlled by applying only part of the deliverable agent at any time. It also means that subsequent doses can be applied using the same device. Alternatively, the independent activation of micropenetrators allows extremely precise treatment, particularly if the whole device is transparent, by allowing the user to, for instance, follow the line of a wound or feature like a wrinkle or scar by pressing on the top of the device. This pressure could then activate the necessary solid micropenetrators into a very specific area of the biological barrier.

In use, one or more micropenetrators are pushed sequentially or in groups so as concentrate the force applied. This can be done by hand or finger, or a variety of powered and manual means, the latter including but not limited to rollers, balls, styli, and blades.

It will, therefore, further be appreciated that the depth of penetration by adjacent micropenetrator arrangements is variable dependent upon the location of the force on the second side of the flexible substrate. Upon application of force upon the second side, the plurality of projections projecting from the first side are capable of penetrating a biological barrier in the locality of where the force is applied. Due to the provision of the flexible substrate the substrate is able to conform to anatomical geometry of the biological barrier. This also means that depth of penetration between adjacent projections are only partially dependent upon each other and due to that inherent flexibility the "bed of nails" effect of spreading the force over a large surface area is reduced.

The provision of the micropenetrator arrangements as defined including first and second projections extending from the head stabilises the projections in use. This means that as the first and second projections contact the biological barrier they do not deflect sideways leading to irregular penetration between micropenetrator arrangements or in the worst case no penetration.

The flexible substrate beneficially comprises a different material to the micropenetrator arrangement.

It will be appreciated that the first and second projection extend to a tip, and the tip may extend through the first side when not in use, or the tip may be retained within the flexible substrate until a force is applied to the second side.

The flexible substrate may comprise a polymeric film, produced for example using organic or silicone monomers. Representative examples include, but are not limited to: polyacrylates, polyurethanes, polydimethylsiloxane or other silicones, cellulose derivatives, hydrogels, hydrocolloids, alginates, polyethylene, polyvinylchloride, polyamides, polypropylene, polytetrafluoroethylene or any fluorinated organic or silicone polymer. These may be gel sheets, foams or films. The flexible substrate is preferably elastomeric and/or elastically deformable. The flexible substrate may comprise a material defining a plurality of recesses or pockets therein for carrying a material such as a drug to be delivered into the biological barrier. The material may take the form of a foam. A preferred substrate material has been found to be silicone rubber.

The flexible substrate may in addition comprise or contain metallic elements, for example titanium, gold or aluminium film.

The first and second projections beneficially project perpendicular to the head. As such, this means that at least two projections beneficially project perpendicular to the head. It will be appreciated, however, that in the event the micropenetrator arrangement comprises additional projections, such additional projections may project diverging away from or towards the first and second projection. The first and second projections beneficially comprise a longitudinal length, and the head beneficially effectively extends substantially perpendicular to the longitudinal length. The micropenetrator arrangement preferably comprises third and fourth projections.

The first and second projections beneficially project from the first side. In one aspect the first and second projections may project from the first side only upon application of a force to the second side.

The first and second projections beneficially project perpendicular to the first side. This improves stability of the projections when pushed into contact with the biological barrier as minimises chance of side to side deflection.

The head may be embedded in the flexible substrate. The second side of the flexible substrate may therefore appear to a user not to include any heads. Alternatively, the head may comprise an abutment surface arranged to abut against the second side. The head ensures that the first and second projection cannot push straight through the flexible substrate avoiding the possibility of the first and second projections being left penetrating through the biological barrier after use.

The abutment surface is beneficially adhered to the second side. The abutment surface may take a variety of forms dependant on the configuration of the head.

The head and the first and second projections are beneficially formed of a single piece of material. It is beneficial that the head and first and second projections are deformed from a single piece of material. It is preferable that the first and second projections are bent to shape. The head and the first and second projections are beneficially formed of a single piece of an elongate rod. The elongate rod is beneficially formed from a wire. The micropenetrator is beneficially in the form of a staple. The head is preferably linear. The first and second projections are preferably substantially parallel.

The head and the first and second projections are beneficially formed of a metallic material. The metallic material may, comprise, copper, silver, zinc and alloys as examples only.

The flexible substrate is preferably transparent.

The head beneficially extends generally parallel to the flexible substrate. The head beneficially extends generally parallel to the second side of the flexible substrate.

The head is beneficially in the form of a cross comprising a first arm and second arm. This provides significant stability to the head such that when a force is applied to the flexible substrate in use the at least first and second projections do not significantly deflect side to side relative to the substrate. It is further preferable that the first and second projection project from the first arm, and a third and preferably fourth projections project from the second arm. The first and second arm are preferably in the form of a cross. It will be appreciated that additional projections may be provided. For ease of manufacture purposes in particular, it is beneficial that the first and second projections projection from distal ends of the first arm and the third and fourth projections project from the distal ends of the second arm respectively.

The first and second arms beneficially comprise an overlap zone of overlapping first and second arms and the first and second arms are beneficially joined at the overlap zones. Accordingly, the micropenetrator in one embodiment may be in the form of a pair of staples where the head comprises the overlapping first and second arm.

The first and second arms are beneficially mutually perpendicular.

It is beneficial that a first and second adjacent micropenetrator arrangement are independent of each other. Accordingly, preferably a first and second micropenetrator arrangement are unsecured relative to each other and are merely in communication via the substrate. The first and second micropenetrator arrangement are beneficially spaced apart. It is further beneficial that the elongate arm of a first micropenetrator arrangement is orientated between parallel to and perpendicular to the elongate arm of the adjacent second micropenetrator arrangement. This is particularly beneficial in a device having a first and second arm in a cross configuration as adjacent micropenetrator arrangements are mounted relative to the substrate to minimise the area that does not comprise a projection. The projections are therefore beneficially spaced apart generally uniformly.

The substrate beneficially comprises silicone rubber. Such a substrate material has been found to provide beneficial properties for the substrate. Such a material is sufficiently flexible and comprises adhesive properties due to their inherent flow ability and as such are capable of adhering to a user's skin which is beneficial if the user's skin is used as the applicator for communicating the device with another area of the skin.

The physical properties of the substrate may be variable between the first side and the second opposing side. This may be achieved through layering the substrate or maybe achieved through treatment of the substrate material. For example, the substrate material may be treated on one side, through for example plasma treating to effect the adhesive properties of the substrate. It is beneficial that the second side of the substrate has a higher level of adhesion than the first side. This means that the substrate adheres to a user's finger which is beneficially used as the applicator whereas will not excessively adhere at the first side, which will usually contact the biological barrier.

The second side is beneficially concave. This may be achieved through treatment of the substrate post manufacture. It is beneficial that such a concave surface means that it is clear for the user which side of the substrate they should contact with their finger and which side is used for the treatment. This is particularly important in this invention due to the small size of the projections, and the possibility for a user to select the incorrect treatment side.

At least a portion of the first and second projection beneficially comprise a curved portion. The curved portion may comprise a plurality of repeating curved portions. Beneficially, the first and preferably the second projection(s) are helical. A benefit associated with the first and preferably second projection being curved is that a liquid such as a drug may be better delivered into the holes made in the biological barrier. Furthermore, it can be hard to get matter to be delivered into the biological barrier such as drugs to stick to the projections typically made of a metal such as steel. The problem that occurs is that the material simply sloughs off when being pushed into the barrier. Accordingly, a solid material such as a solid drug may be adhered to the curved portions improving the capability of delivery through the biological barrier. The curved portions allow for spaces, lacunae or pockets for solid or semi solid or liquid drug etc to inhabit. The repeating curved portions are beneficially achieved through twisting of the first and preferably second projection. This improves the capability to carry material.

Alternatively or in addition in order to provide improved capability of carrying a material into the biological barrier, there may be a supplementary projection arranged such that at least one of the first and/or second projection are in communication with the supplementary projection for penetration of a biological barrier. The supplementary projection is preferably in physical communication with the first and/or second projection. Preferably, the supplementary projection is adjacent to the first and/or projection. Beneficially, in one embodiment the supplementary projection may be wrapped around at least one of the first and/or second projection. Beneficially, each of the first and secondary projections are in communication with a supplementary projection. Beneficially, the supplementary projection comprises a first and second supplementary projection element having a head portion therebetween, the first and second supplementary projection elements arranged to communicate between the first and second projections respectively. The purpose of a supplementary projection is to aid in transfer of any solid of liquid through the biological barrier. A drug may be solid or liquid may, for example. The supplementary projection is beneficially intertwined with at least one of the first and/or second projections.

The first and second projections beneficially extend to a penetration tip, at least one of the first and second projections comprising a cavity therein extending to an opening adjacent the tip. The opening at the tip is defined by an edge that may be non-uniform. This may be achieved by cutting the projection at an angle to the longitudinal length to aid penetration in to the biological barrier. It will appreciated that the cavity may be sealed prior to application and the opening is formed upon application of pressure to the flexible substrate.

In one embodiment, the first side of the flexible substrate may carry a drug or biological active material therein. This means that upon application on to the biological barrier the first and second projection penetrate the biological barrier and the drug or biological material carried on the first side may be delivered through the openings provided by the first and second projections.

In one embodiment, the first and second projection may comprise a drug or biologically active material deposited thereon.

The surface of the first side of the flexible substrate may be undulated, having a plurality of recesses for receipt of a drug or biological material.

The surface of the first side of the flexible substrate may be pre formed to take the form of the anatomical geometry of the part the biological barrier. For example, the first side of the flexible substrate may be contoured to seat beneath a user's eye. The substrate may itself have a first side contoured to seat onto the surface of an eye itself, where the eye is the biological barrier.

A plurality of micropenetrators may be co-joined by their respective heads. The heads effectively therefore form a frame work. The formation of co-joined heads may effectively form a layer adjacent to the second side of the flexible substrate.

A bridge portion is beneficially provided extending between micropenetrator arrangements. The bridge may be arranged to fracture upon application of a force in the direction of the second side, accordingly, a plurality of micropenetrator arrangements may be joined together. The number may be as small as two, but may be significantly greater in number. In one embodiment, the micropenetrator arrangements comprise staple configurations which are joined to other staple configurations to form a unit. The provision of a network of co-joined heads overcomes a significant problem associated with working with a flexible substrate, being that the micropenetrators can simply fall to the side when pushed rather than penetrating the biological barrier. Such a configuration creates a small area that is stiff and cannot be easily pushed over. The formation of co-joined heads can be achieved through manufacture of a single large micropenetrator arrangement or alternatively through bonding together of a plurality of smaller micropenetrator arrangements.

Other examples of means to join together micropenetrator arrangements into a unit include but are not limited to a rigid structure formed using injection moulding, moulding and curing, wire forming, bending, stamping, cutting, milling, 3D printing. The rigid structure may be bonded to the flexible substrate, or may be only connected to the at least one micropenetrator. The rigid structure also limits the lateral or rotational movement of the micropenetrators, and protects the second side from being damaged.

The flexible substrate may further comprise a micropenetrator carrier layer positioned adjacent the second side, the first and second projections extending from the carrier layer. The carrier layer may be stiffer than the flexible substrate. This means that the flexible substrate can be made more flexible to more easily conform to the anatomical geometry of the biological barrier whilst the carrier layer ensures rigidity of the device. The carrier layer may comprise a matrix wherein the matrix may comprise a plurality of openings therein. This increases the stiffness of the head of the micropenetrator arrangement. The matrix beneficially allows flexibility of the bridges between portions of the carrier layer that carry the heads.

A formation may be provided defining a cavity therein positioned above the head of a micropenetrator arrangement. This provides a way of increasing the applied force to the first and second projections. The cavity may burst upon application by force thus increasing the speed of application of the force. This is analogous to 'bubble wrap' packaging, where sudden breakage of the bubble membrane causes rapid acceleration of the finger.

The flexible substrate may comprise a formation positioned above the head of the micropenetrator arrangement, the formation comprising a material of higher rigidity than the flexible substrate. The flexible substrate may comprise a formation positioned above the head of the micropenetrator arrangement, the formation protruding from the second side of the flexible substrate. Convex formations may be provided, which may snap into a concave formation on the application of external force thereby increasing the speed of application of the projection(s) to a user.

The device may be applied to skin by force applied directly from a user's fingers for example, or a mechanical applicator may be provided a part of the device to apply a mechanical force. For example, the device may be provided on a roller and retained on the roller or rolled off to leave the device on the skin. Other mechanical applicators are envisaged such as the provision of an energy storage device such as a spring or elasticated element to store and rapidly apply force. Compressed gas or a liquid may be the source of application of the force.

Also according to the first aspect of the present invention there is a method of providing a cosmetic treatment to a biological barrier, comprising the steps of:
  positioning a device as hereinbefore described adjacent a biological barrier;
  applying a force to the second side of the device to cause the first and second projections to penetrate the biological barrier.

The device is preferably positioned in contact with a biological barrier. Preferably, the second side is positioned in contact with the biological barrier.

Also according to the first aspect of the present invention there is a method of delivering an agent across a biological barrier comprising the steps of:
  positioning a device as hereinbefore described adjacent to a biological barrier, the device carrying the agent to be delivered;
  applying a force to the second side of the device to cause the first and second projections to penetrate the biological barrier and deliver the agent through the biological barrier.

The device is preferably positioned in contact with a biological barrier. Preferably, the second side is positioned in contact with the biological barrier.

The first and second projections may have different diameters to each other. First and second projections also may have different lengths, so as to penetrate to different depths, or to enable penetration of one part of the device before another part.

The first and second projections may be needle-shaped, pointed, chisel shaped or knife-edged. In a preferred embodiment, the micropenetrators are formed of wire, cut at an angle not perpendicular to the longitudinal length of the projection. The wire may be bent into a staple shape and this is pressed into the flexible membrane. The wire can be of practically any cross-sectional shape, including round, rectangular, triangular and may comprise a flat strip.

Micropenetrators can be formed in a variety of ways, including but not limited to wire cutting, moulding, embossing, extruding, drawing, stamping, etching and machining. They may be formed individually, or as a unit of two or more connected together. If connected together, the micropenetrators may be subsequently made wholly or partially independent by modifications such as cutting, machining, stamping, weakening, etching, laser cutting of some or all connecting pieces.

The first and second projections may protrude from the surface of the flexible substrate, or they may be embedded within the flexible substrate, only leaving the surface on the application of force to the second side. Alternatively, the first and second projections may be at least partially surrounded by a tube or sheath that is itself embedded within the membrane. The length of protrusion may be altered for different types or treatment to allow deeper or shallower penetration, for instance in professional skin treatment the perforators may need to enter the skin to a depth of 1 mm or more. Hence, first and second projections may protrude from the first side of the device for between 3 mm and 0 mm, although more preferably between 1.5 mm and 100 µm.

The first surface of the device may be structured in a non-flat arrangement, so that dips, protrusions, channels or other topography appear in the biological barrier contact layer. These dips may correspond in some areas to the tips of micropenetrators. The dips or cup shapes may aid penetration of the projections, or may be useful to impede the movement of fluid and hold it close to the micropenetrators.

The first and second projections may also be treated or shaped to allow fluid to flow down or wick along their length, to move fluid containing actives from one area to another. This could be to supply liquid to the tips or hole made by the tips, or conversely to move liquid from the tips to a more distal location. To this end, the micropenetrators include a porous or wicking material or, alternatively, a hollow tube or series of tubes. In a further embodiment, two wires or similar structures can be wound together or closely approximated to form a fluid pathway in the join.

A second aspect of the present invention will now be described. It is noted that features defined with respect to the first aspect may also be beneficial for the second aspect.

According to the second aspect of the invention there is a device for penetration of a biological barrier, the device comprising a substrate having a first layer carrying a plurality of projections for penetrating a biological barrier extending therefrom and a flexible second layer comprising an outwardly facing surface, wherein the plurality of projections extend at least partially through the second layer towards the outwardly facing surface.

It will be appreciated that the plurality of projections project from rearwardly of the outwardly facing surface. The outwardly facing surface preferably comprises a skin contact surface.

It is further beneficial that the micropenetrator arrangement takes the form as described with respect to the first aspect, as does the substrate material and configuration.

It will be appreciated that the flexible second layer is capable of conforming to the anatomical geometry of a biological barrier. Furthermore, it will be appreciated that in use the plurality of projections extend outwardly from the outwardly facing surface of the second layer. When not in use, however, the plurality of projections do not necessarily stand proud of the flexible second layer. The tips of the plurality of projections may terminate within the flexible second layer until a force is applied to the first layer.

The benefit associated with the second aspect of the present invention is that as the first layer carries a plurality of projections these projections are stabilised to limit side-to-side deflection as force is applied to the first layer. The second layer, however, acts to conform to the anatomical geometry of the skin.

The first and second layer beneficially comprise different materials, wherein the second layer is preferably thicker than the first layer. The projections beneficially extend substantially perpendicular to the first layer.

The first layer beneficially comprises a plurality of first zones having a projection extending therefrom, and plurality of second zones intermediate the first zone. The first layer may form a matrix having a plurality of projections extending therefrom. The second zone beneficially comprises web portions extending between first zones. It is beneficial that the web portions have a lower stiffness than the first zones. It is beneficial that there is inherent flexibility in the web portions meaning that application of force upon the first layer selectively activates those projections underneath and adjacent the applied force partially independently of other projections.

The second zone beneficially further comprises a plurality of apertures therein. Such a configuration of a first layer provides sufficient stiffness in order that the projections do not deflect side-to-side upon an applied force however the provision of the web portions and preferably apertures provide sufficient flexibility for the applied treatment.

The projections may each further comprise a head, wherein the head is carried by the first layer. The head may comprise an abutment surface and the first layer may comprise a top surface facing away from the second layer, the abutment surface arranged to abut against the top surface of the first layer. In an alternative embodiment, the head may be embedded in the first layer. Alternatively, the projections may be integrally formed with the first layer.

Also according to the second aspect of the invention there is a method of providing a cosmetic treatment. The second aspect of the invention comprises a method of providing a cosmetic treatment to a biological barrier, comprising the steps of:
positioning a device as hereinbefore described adjacent to a biological barrier;
applying a force to the first layer of the device to cause the projections to penetrate the biological barrier.

The device is preferably positioned in contact with a biological barrier. Preferably, the second side is positioned in contact with the biological barrier.

Also according to a second aspect of the invention there is a method of delivering an agent across a biological barrier comprising the steps of:
positioning a device as hereinbefore described adjacent a biological barrier, the device carrying the agent to be delivered;
applying a force to the first layer of the device to cause the projections to penetrate the biological barrier and deliver the agent through the biological barrier.

The device is preferably positioned in contact with a biological barrier. Preferably, the second side is positioned in contact with the biological barrier.

A third aspect of the present invention will now be described.

According to a third aspect there is a device for penetration of a biological barrier, the device comprising a flexible substrate having a first side and a second opposing side, the device further comprising a plurality of micropenetrator arrangements each comprising a head and a projection extending from the head to a tip for penetrating a biological barrier, wherein the projection at least partially extends through the flexible substrate towards the first side and is at least partially curved intermediate the head and the tip.

The flexible substrate is preferably configured to be conformable to the anatomical geometry of the biological barrier. The first side preferably forms a biological barrier contact surface. The configuration of the micropenetrator arrangement and substrate beneficially takes the form as described with respect to the first aspect.

Upon application of a force to the second side of the flexible substrate the projection projects from the first side. The projection penetrates a biological barrier accordingly. In one embodiment the projection only projects from the first side upon application of a force to the second opposing side. In an alternative embodiment, the at least the tip of the projection may extend from the second opposing side irrespective of whether any force is applied.

The projection beneficially projects from the first side.

The provision of a projection being at least partially curved intermediate the head and the tip aids in delivery of drugs or other biologically impacting material through the biological barrier. Solid material is better retained on curved portions and liquid is better delivered through the holes made through the biological barrier.

The curved portion beneficially comprises a plurality of repeating curved portions. It is beneficial that the projection is twisted. The projection may be helically wound.

A supplementary projection may be provided for penetrating a biological barrier arranged such that projection is in communication with the supplementary projection for penetration of a biological barrier. The supplementary projection is beneficially in physical communication with the projection. The supplementary projection is preferably at least partially curved. The supplementary projection may be wrapped around the projection and beneficially extends from the head. The supplementary projection may be intertwined with the projection.

It will be appreciated that preferred features of the third aspect of the invention have been described elsewhere with respect to the first and second aspect. The third aspect may comprise a plurality of projections extending from the head. It will be understood, however, that a single projection extending from each head may be provided capable of features described with respect to the first and second aspect. For example, the provision of a cavity within the projection, and the features of a projection carrying a drug or biologically active material may be provided as examples only.

According to the third aspect of the invention there is a method of providing a cosmetic treatment to a biological barrier, comprising the steps of:
positioning a device according to any of claims 38-49 adjacent a biological barrier;
applying a force to the first layer of the device to cause the projections to penetrate the biological barrier.

According to the third aspect of the invention there is a method of delivering an agent across a biological barrier comprising the steps of:
positioning the skin contact surface of a device according to any of claims 38-49 adjacent a biological barrier, the device carrying the agent to be delivered;
applying a force to the first layer of the device to cause the projections to penetrate the biological barrier and deliver the agent through the biological barrier.

The device of aspects of the present invention can be used for diagnostic purposes, for the delivery of agents such as allergens for patch testing, the response to which allows a physician to determine the presence of absence or course of a disease state. Alternatively, the micropenetrators can be used to create a pathway from the skin to a device which analyses the body fluid (extra cellular fluid) to determine levels of a chemical, such as glucose.

In one embodiment, the micropenetrators comprise hollow tubes. These can be cut at an angle to aid penetration in to the biological barrier. The tubes can be a continuous staple shape to form a microperforator unit, and in addition/or may be joined to other micropenetrators to form a micropenetrator unit by a different joining means. This joining means can be formed in situ or may be preformed by a variety of means including but not limited to injection moulding, pressing, stamping or cutting. The hollow tubes may be open at the distal end to allow flow of liquid or gas down the tube, or they may be closed. The tubes may contain liquid or solid, or any other formulation including suspensions and gels. This liquid or solid can be released into or through the biological barrier via pressure, or more passively by capillary action, diffusion, osmosis, dissolution, swelling etc. The projections are practically any size, from nanometres up to millimetres in height. Most preferably they are between 100 µm and 4000 µm in length. They are of practically any density (numbers of implants per $cm^2$), from 1 projection per device, to many thousands per $cm^2$. The device itself may be any size or shape, for example it may be circular, ovoid, or in a strip shape.

The device according to the invention is intended for application to a "biological barrier". As used herein, the term "biological barrier" refers to any biotic surface that separates a human or animal body from the environment and may include skin (including scalp), eye, mouth-lining, nasal passages, gums, glans penis, external female genitalia, or a wound or incision. The "biological barrier" may comprise epithelial tissue, such the skin and/or mucosa, and may further include broken skin as examples only. As used herein, the term "skin" is to given its usual meaning in the art, i.e. the epithelial tissue providing an anatomical barrier between the internal and external environment of the body. The skin is preferably exposed to form the outer surface of the body. The outer-most layer of the skin, that is usually traversed using a device according to the invention, is known as the stratum corneum.

Delivery of an agent across the skin is referred to in the art as "transdermal delivery". The device according to the invention is therefore useful for transdermal delivery.

The device according to the invention is useful in both veterinary, i.e. animal health, and medical, i.e. human health applications. The device can further be used in a purely cosmetic method, for example to deliver agents that are intended to improve appearance only, and do not have a therapeutic effect. The invention therefore includes cosmetic methods. Cosmetic agents include, but are not limited to dermal/epidermal fillers such as hyaluronic acid, botulinum toxin or coloured compounds for semi-permanent make-up, tattooing or identification.

It is also clear that the device according to aspects of the invention can be used with no active agents, purely to create microwounds in the biological barrier. In the skin, microwounds trigger a healing response and are used for collagen induction, scar treatment and other cosmetic treatments.

Aspects of the invention are concerned with the delivery of agents across a biological barrier. One embodiment of the invention involves delivery of a vaccine. The term "vaccine" is well known in the art to refer to an agent that is used to establish or improve immunity to a particular disease. A vaccine can be prophylactic or therapeutic and may include conventional and DNA vaccines. In a preferred embodiment, the vaccine is prophylactic to prevent or ameliorate the effects of future infection.

Aspects of the present invention also can be used to transmit energy to or through the biological barrier. This can be useful in creating structural changes in the barrier, such as by ablation, coagulation, heating etc. Energy can be of any type, including but not limited to electrical energy, radio-frequency energy, heat or cold, electromagnetic energy including light. Energy can also be used for sensing and diagnostic purposes. The device in one embodiment includes a means for determining penetration depth, such that an action is only triggered at a prescribed depth of penetration into the biological barrier. In another embodiment the micropenetrator/microperforator arrangement or projection(s) thereof is sheathed or protected for some of its length, or until a penetration depth. This may protect the biological barrier from energy damage in unwanted areas. The projections may contain a focussing or transmission means, such as a fibre optic filament or a mirror or reflective surface within the microperforator. Light may be supplied down the microperforators for diagnosis or treatment, this may be advantageous to spare the top layers of a biological barrier, and when the outermost layers of a biological barrier make an unwanted barrier to light or other energy which would reduce the intensity of the effect or signal, for instance by refraction or reflection. The energy may also be used to create a temporary stimulation to the biological barrier, or to help active compounds to enter or leave the biological barrier, for example using iontophoresis.

The device may comprise a composite of layers, through which at least one has the microperforators partially or full embedded within. It is considered useful if the layer nearest the skin is adhesive, or is adhesive in some areas. Representative adhesives for use on the skin include acrylate, hydrogel and silicone adhesives. This may have utility in reducing the ability of the biological barrier to deform under pressure and thereby resist penetration of the microperforators. On this side it is more advantageous if the outermost layer is non-adhesive, and more preferably low friction.

The flexible substrate may comprise or contain a transdermal patch, of which a number of designs are known, including reservoir, matrix and drug in adhesive. The device may alternatively or in addition contain microfluidic channels for passage of liquid to or from the biological barrier. The device may contain a reservoir that contains a mixing means, or a biologically active agent in a dry form which can be reconstituted by addition of exogenous liquid or liquid held within the device.

A layer within the device may also be used to hold liquid or accept exogenous liquid such that in use liquid from this layer is passed down towards the biological barrier via the microprojections or other holes.

In an alternative description there is a device for contact with a biological barrier containing micropenetrators which in use penetrate said biological barrier, comprising of at least one flexible layer, microperforators with a sharp edge or point which at least partially extend through the at least one flexible layer such that when force is applied to the distal side of the device, the microperforators are pushed into the biological barrier, the micro penetrators being composed of a different material to the flexible layer and where individual or groups of micro penetrators can move independently of other micropenetrators, and the distal side of the micropenetrators is significantly larger than the proximal side, either by virtue of being attached to other micropenetrators or by forming or being connected to a larger structure.

The or each micropenetrator may be made from metal.

The micropenetrator may be formed from wire.

The micropenetrator may be flattened in cross section.

The at least one micropenetrator may be shaped into a pointed edge.

The at least one micropenetrator may be blade or chisel shaped.

The projections may be of equal length of penetration into the biological barrier or body.

The projections may be not of equal length.

The microprojections may be twisted.

The microprojections may comprise multiple metal strips or wire conjoined.

The at least one microprojections may comprise two or more elements twisted around each other.

The microperforators may be staple shaped.

The microperforators may comprise more than one staple in close proximity or touching.

The microperforators may be bonded to at least one flexible layer of the device.

More than one microprojection or staple may be bonded together to form a unit.

At least one flexible layer may be elastomeric or elastically deformable.

Multiple layers may be stacked in a parallel manner.

There may exist a lacuna, foam or other fillable space between or within the stacked layers where a liquid or gel can be disposed or injected, such that the liquid can pass adjacent or via the microprojections and thence into or onto the biological barrier.

The at least one layer may contain a drug or biological active retaining layer.

The liquid may flow down adjacent to the microprojections and thence be deposited in the or onto the biological barrier.

The layers may contain or comprise a transdermal patch.

Energy may be transmitted through the microperforators.

The energy may be electrical or thermal energy.

The at least one microperforator may be associated with a hollow structure that is at least partially embedded in the flexible membrane such that in use the microperforator passes through the hollow structure.

The hollow structure may contain a solid or liquid that can enter the biological membrane by diffusion or direct injection.

A drug may be deposited on or coated onto the at least one microperforator, either in solid, liquid or gel form.

The movement of the microperforators may be caused by one of: a pressure activated breakage such as a membrane breaking, a conformational change such as changing from convex to concave, a spring or other biasing means, electromagnetic force, a roller, a stylus, squeegee or an external mechanical applicator.

In another definition there is a method of delivering an agent across a biological barrier, comprising the steps of:
a. contacting the biological barrier with a device according to any one of the preceding claims comprising the agent to be delivered; and
b. activating the means for providing a motive force to the or each solid microperforator.

The agent may be a cosmetic agent.

The invention may be for use in therapy, wherein the therapy may be vaccination, where the therapy may be amelioration of scars.

Aspects of the present invention will now be described by way of example only with reference to the accompanying drawings in which:

FIG. 11 is a further schematic representation of a device according to an exemplary embodiment relative to a finger.

Figure 1A:
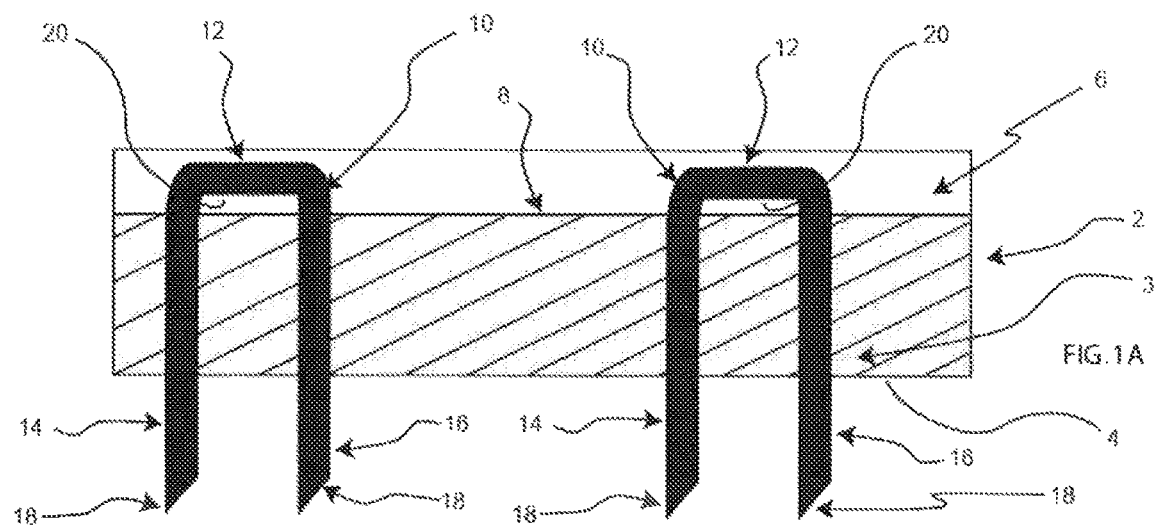
FIGS. 1a and 1b show an exemplary embodiment of a device according to aspects of the present invention prior to activation in FIG. 1a and during activation in FIG. 1b.

Referring to FIG. 1a a device according to an exemplary embodiment of the present invention is presented. The device 2 is presented prior to activation and contact with a biological barrier 5. The device 2 comprises a flexible substrate 3 having a biological barrier contact surface 4. In the embodiment presented a supplementary layer 6 is provided on the second opposing side 8 of the flexible substrate. Presented in this embodiment for clarity purposes are two micropenetrator arrangements 10 each comprising a head 12 and first and second projections 14, 16. The projections extend to a tip 18 and in the form presented are sharpened to a point through cutting the respective projections at an angle non-perpendicular to the longitudinal length of the respective projections. The head 12 comprises an abutment surface 20 which may abut the second side 8 of the flexible substrate 3. In the embodiment presented, due to the provision of the supplementary layer 6 the head 12 is encapsulated within the layer 6. Also in the embodiment presented, the projections 14, 16 project from the first side 4 ready for penetration into the biological layer 5. Such projections may be retained within the flexible substrate 3 adjacent to the first side 4 such that upon application of a force causes the tips 18 to penetrate through the first side 4 and into the biological barrier 5.

The layer 6 presented in FIG. 1 in combination with the projections 14, 16 extending towards the first side 4 of the flexible substrate 3 retain the micro-penetrator arrangements 10 in position.

Figure 1B:
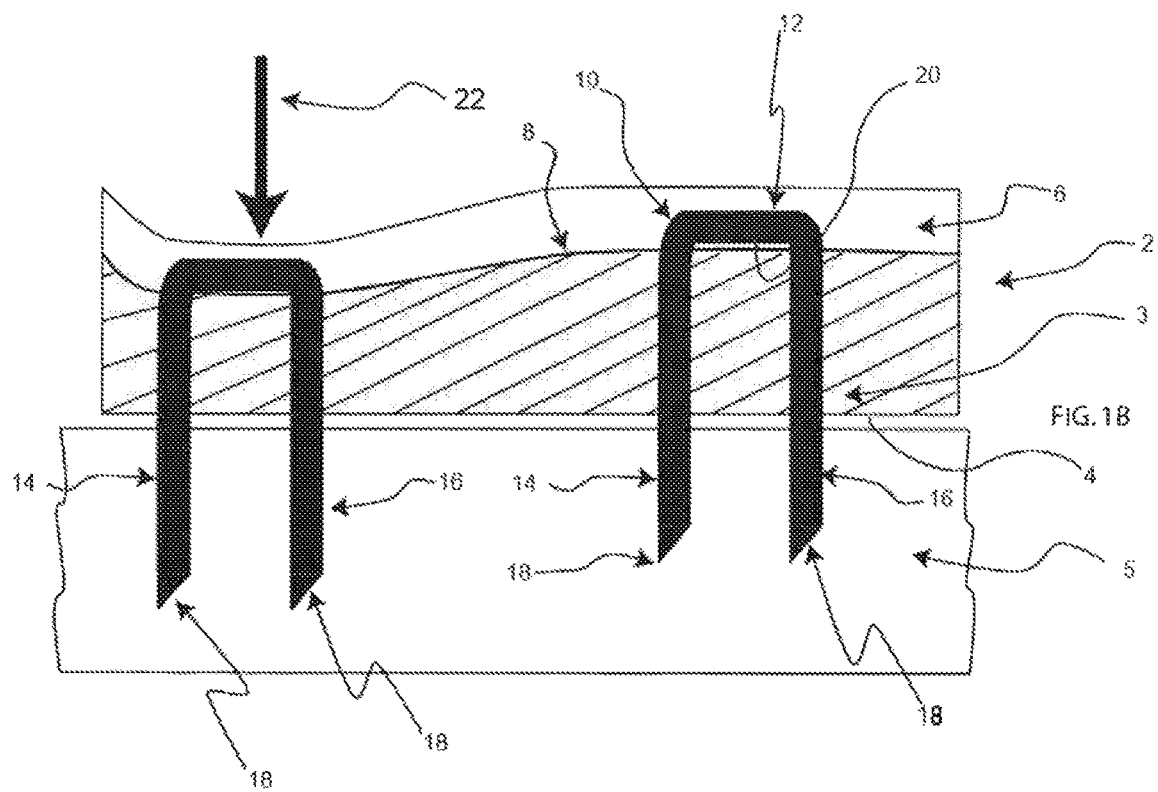

As shown in FIG. 1b, as a force is applied as indicated by arrow 22 a micro-penetrator arrangement 10 is forced downwardly through the biological barrier 5. Due to the flexibility inherent in the flexible substrate 3 the depth of penetration by micropenetrator 10 is different to an adjacent micropenetrator arrangement. Accordingly, treatment can be tailored to the precise location required. As also shown in FIG. 1b, the force applied in the direction indicated by arrow 22 causes the micropenetrator arrangement 10 to enter straight into the biological barrier 5. Side-to-side deflection is minimised due to the provision of the head 12 and plurality of projections 14, 16 extending therefrom. Stability is further improved through the provision of additional projections extending from the head as described in more detail with respect to FIG. 2. The flexible substrate 3 is preferably elastomeric as is the supplementary layer 6 if present. The force identified in the direction indicated by arrow 22 can be supplied by a roller, a vibrator or any other form of power, and can be used to actuate either a small number of micropenetrator arrangements 10 or a single one. Alternatively, a large number may be activated in parallel or all the micropenetrators in a single device. The micropenetrators may be driven by the force in sequence or at random, and over any time period.

Figure 2A:
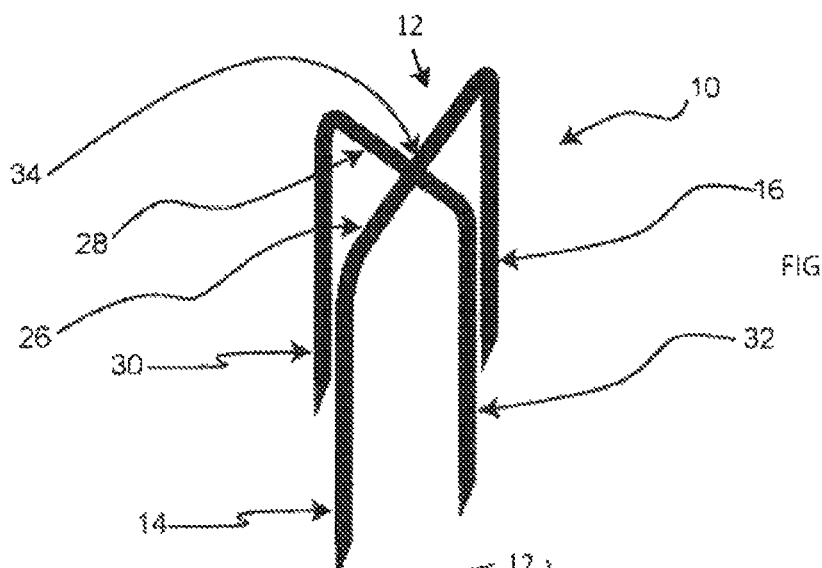
FIG. 2a is a schematic representation of a micropenetrator arrangement without the substrate shown for clarity purposes according to an exemplary embodiment of the present invention.

The head 12 and the first and second projections 14, 16 are beneficially formed of a single piece of material. The material is preferably metallic and the first and second projections 14, 16 extend substantially perpendicular to the head 12. The micropenetrator arrangement as presented in FIG. 1 is in the form of a staple where the projections 14, 16 are of equal length however it will be appreciated that this is not essential. Referring to FIG. 2, an exemplary micropenetrator arrangement is presented. The micropenetrator arrangement 10 comprises a head 12 in the form of a cross comprising a first arm 26 and second arm 28. First and second projections 14, 16 extend from the distal ends of the first arm 26. From the distal ends of the second arm 28 third and fourth projections 30, 32 extend. The benefit associated with additional projections extending from the head 12 is the further stability provided. It will be appreciated that a configuration of three or more projections provides improved stability. In the embodiment presented, the arms 26, 28 overlap at an overlap zone 34 and are beneficially adhered at this point. First and second arms 26, 28 are mutually perpendicular.

Figure 2B:
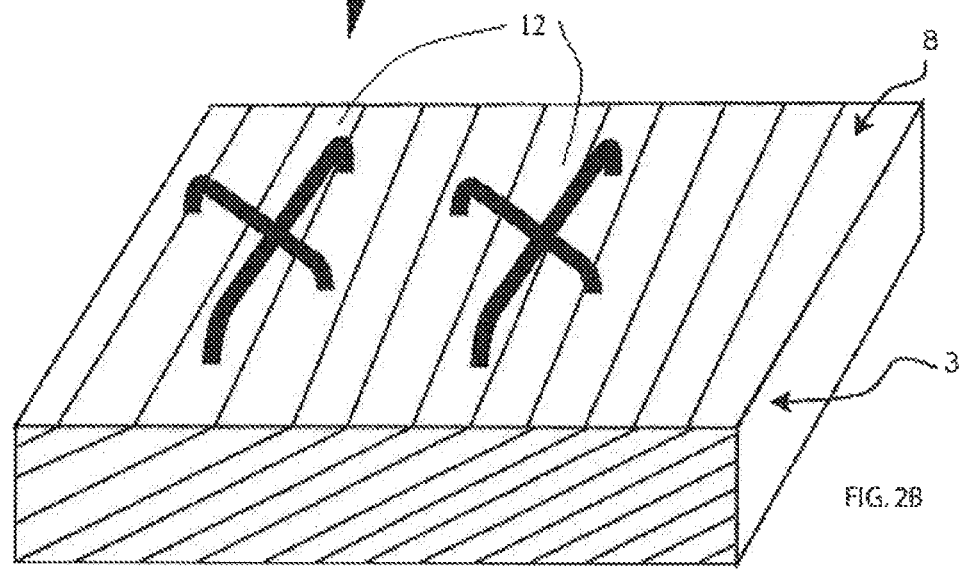
FIG. 2b is a schematic upper perspective view of a device according to an exemplary embodiment of the present invention.
Figure 2C:
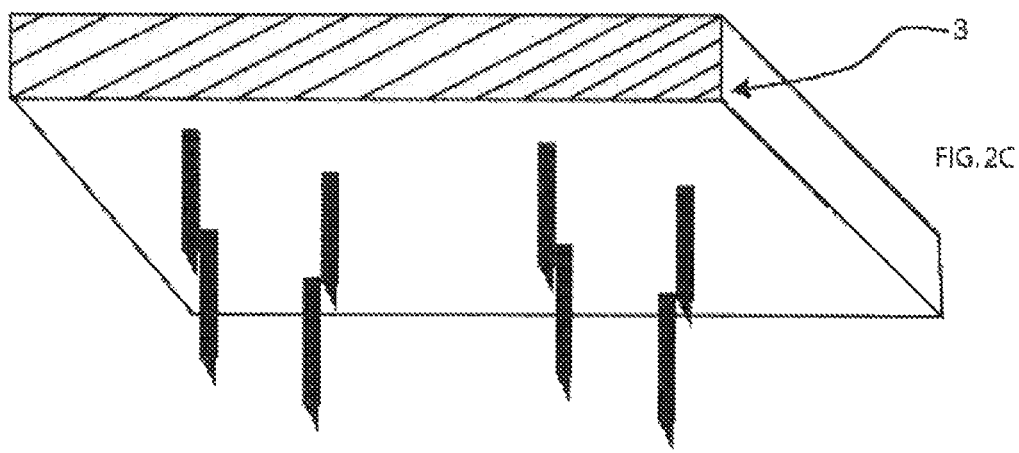
FIG. 2c is a schematic underside perspective view of the embodiment as presented in FIG. 2b.

Referring to FIG. 2b, the head 12 can be seen abutting the second side 8 of the flexible substrate 3. In bottom perspective view as shown in FIG. 2c, the projections 14, 16, 30, 32 project through the flexible substrate 3 for penetration into a biological barrier 5.

Figure 3A:
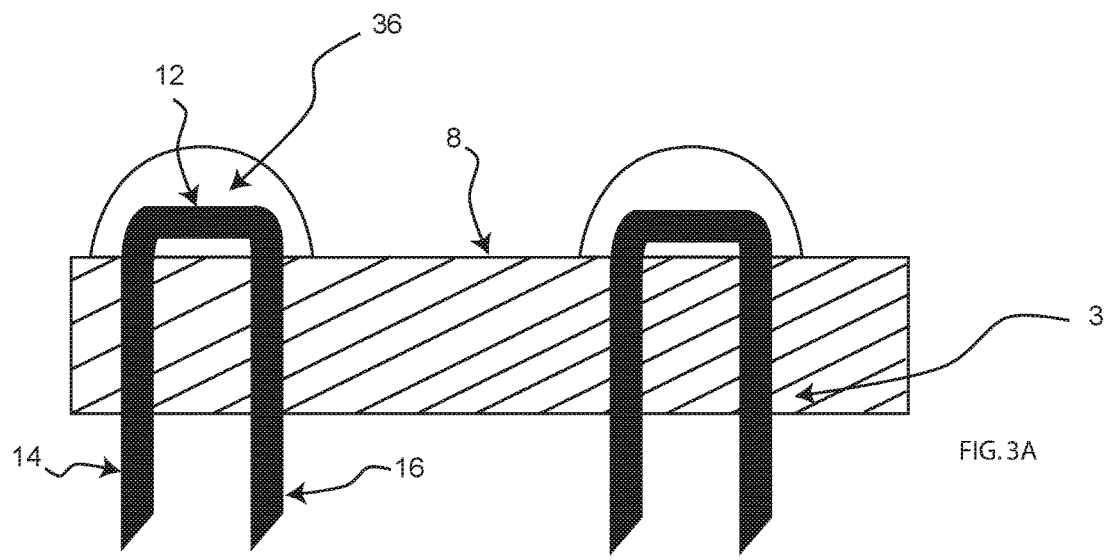
FIGS. 3a and 3b are an alternative exemplary embodiments of the present invention in a configuration prior to activation as shown in FIG. 3a and in a configuration during activation as shown in FIG. 3b.
Figure 3B:
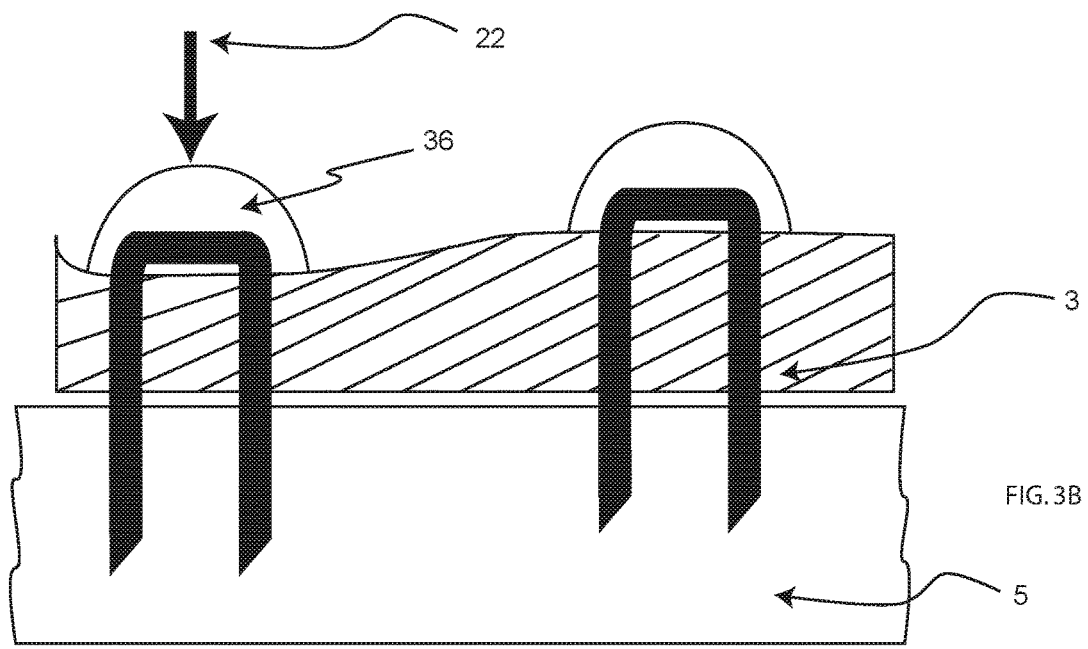

Referring now to FIGS. 3a and 3b an embodiment of the present invention is presented wherein the micropenetrator arrangement comprises two projections 14, 16 and head 12. It will be appreciated, however, that such a micro-penetrator arrangement 10 has been presented as an example only and a single projection may be utilised with a head 12. The single projection may be at least partially curved. Provided is a formation 36 positioned above the head 12. The formation 36 may be adhered to the head 12 and also to the second side 8 of the flexible substrate 3. The provision of this formation reduces the lateral freedom of movement of the micropenetrator 10. Referring to FIG. 3b the activation sequence is shown pushing the micropenetrator 10 into the biological barrier 5 and shown is the minimal side-to-side deflection of the first and second projections 14, 16. It will be appreciated that the formation 36 protrudes from the second side 8 and in the embodiment shown is in the form of a dome. It will also be appreciated, however, that other shape formations are possible. It will further be appreciated that it is beneficial that the formation 36 comprises a material of higher rigidity than the flexible substrate 3.

Figure 4:
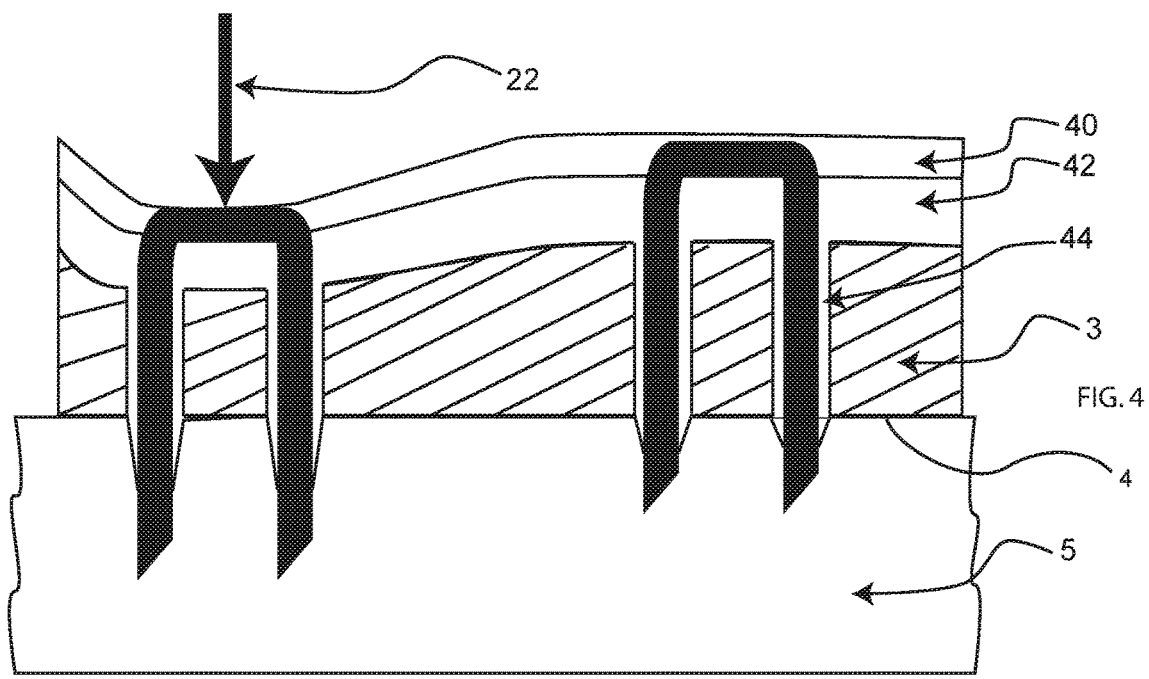
FIG. 4 is a schematic side view of an exemplary embodiment of the present invention with the micropenetrator arrangement during activation.

Referring to FIG. 4, a further exemplary embodiment of the present invention is presented. Again, a micro-penetrator arrangement 10 has been shown comprising a configuration of a head 12 and first and second projections 14, 16. It will be appreciated that the head may take a variety of forms and any number of projections may be utilised. In the embodiment of FIG. 4 the head 12 is provided within a layer 40 which is flexible. In the embodiment shown the head 12 is provided within the layer 40 however it will be appreciated that the head 12 may be provided abutting the layer 40 such that the projection(s) extends therethrough. Provided intermediate the layer 40 and the flexible substrate 3 is a cavity 42 that may be filled with a liquid. Channels 44 may extend through the flexible substrate 3 through which the projections extend providing a flowpath through the flexible substrate 3 to the first side 4. Upon actuation as shown in FIG. 4, fluid may travel from the cavity 42 through the channels 44 and into the biological barrier 5. The increase in pressure caused by the force applied as indicated by arrow 22 further pushes the liquid down the channels 44 and into the biological barrier.

Figure 5A:
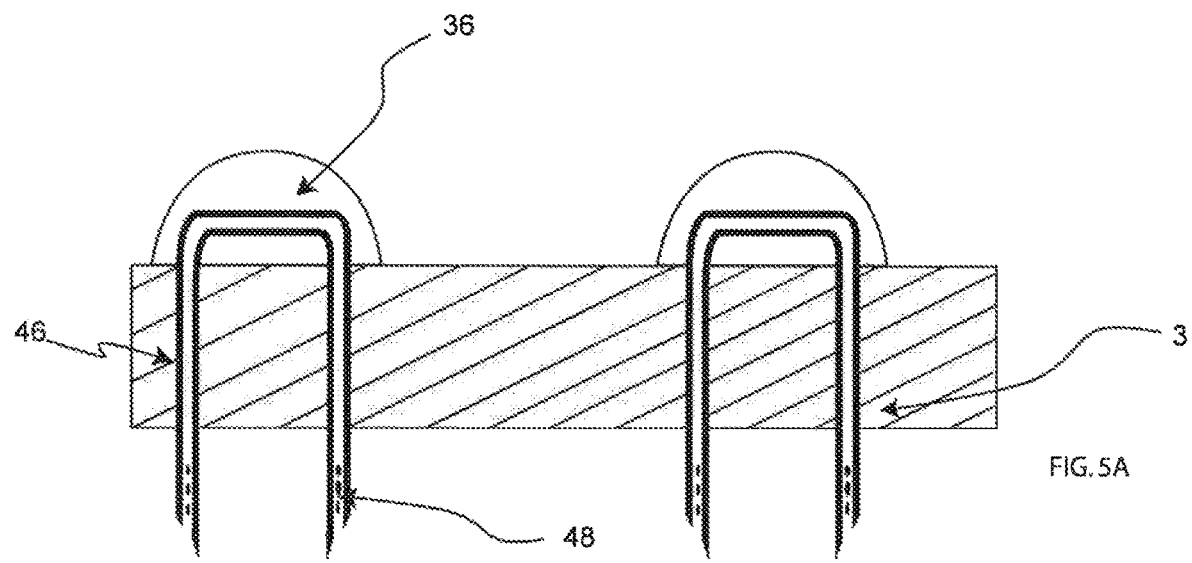
FIGS. 5a and 5b are further exemplary embodiments of the present invention in non-activated and activated configurations as shown in FIGS. 5a and 5b respectively.
Figure 5B:
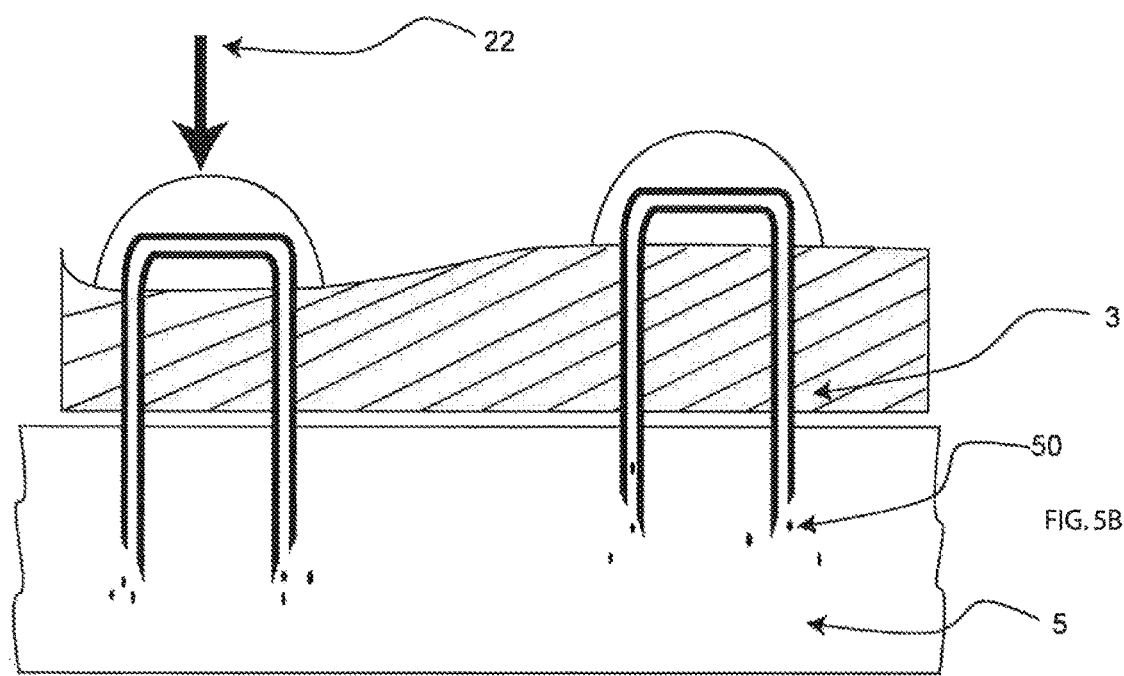
Figure 6A:
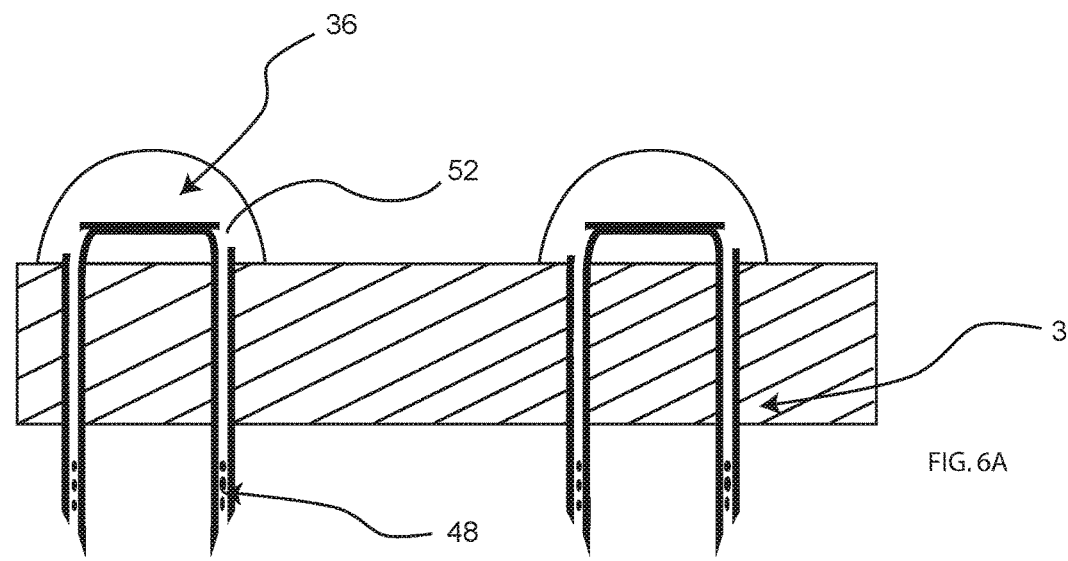
FIGS. 6a and 6b are further exemplary embodiments of the present invention in the non-activated and activated configurations according to a further exemplary embodiment.
Figure 6B:
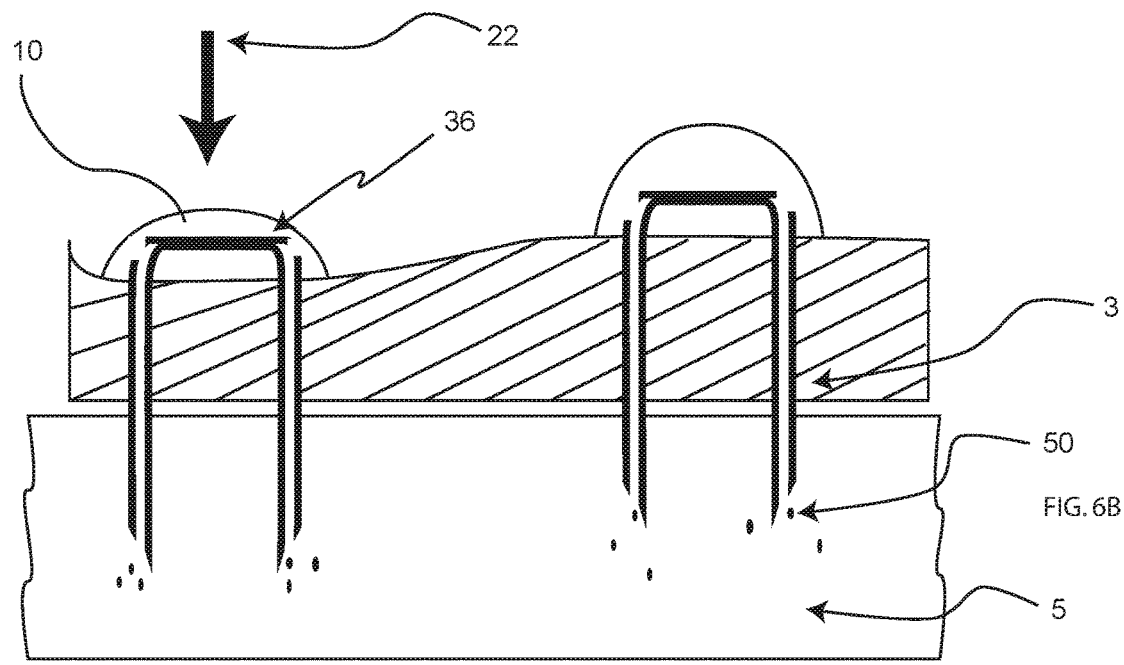

Referring now to FIG. 5 a further embodiment of the invention is presented. In this embodiment, the projections 14, 16 have cavities therein and are provided such that the cavities are in fluid communication with each other via the head 12. A formation 36 may be provided as described with respect to FIG. 3 to focus pressure and to reduce lateral motion of the micropenetrator within the flexible substrate 3. Within the cavities 46 are injectates 48. These injectates may be solid or liquid or any other formulation. FIG. 5b shows the device in actuation on a biological barrier such that under the effect of force 22 the projections 14, 16 are driven into the biological barrier. Once there, the injectates dissolve and leave the cavities 46 becoming semi-dissolved particles 50. FIG. 6 presents a similar embodiment however provided is an additional opening 52 providing access to the cavities. The cavity is beneficially open at more than one point to allow a flow of material therethrough. In FIG. 6a hollow tubes for the projections and head are presented and disposed therein are injectates 48. Presented in this embodiment, whilst also applicable to any other embodiment, are formations 36 arranged to be deformable. These may be the same or similar configuration to formations 36 as presented with respect to FIG. 3 however in this embodiment the key difference is that they are deformable. Within them there may be a cavity. Accordingly, injectates 48 may be forced from the cavity 46 to enter the biological barrier 5. The formation 36 as shown in FIG. 6b can be seen to have collapsed thus imparting additional force to the micropenetrator arrangement 10.

Figure 7:
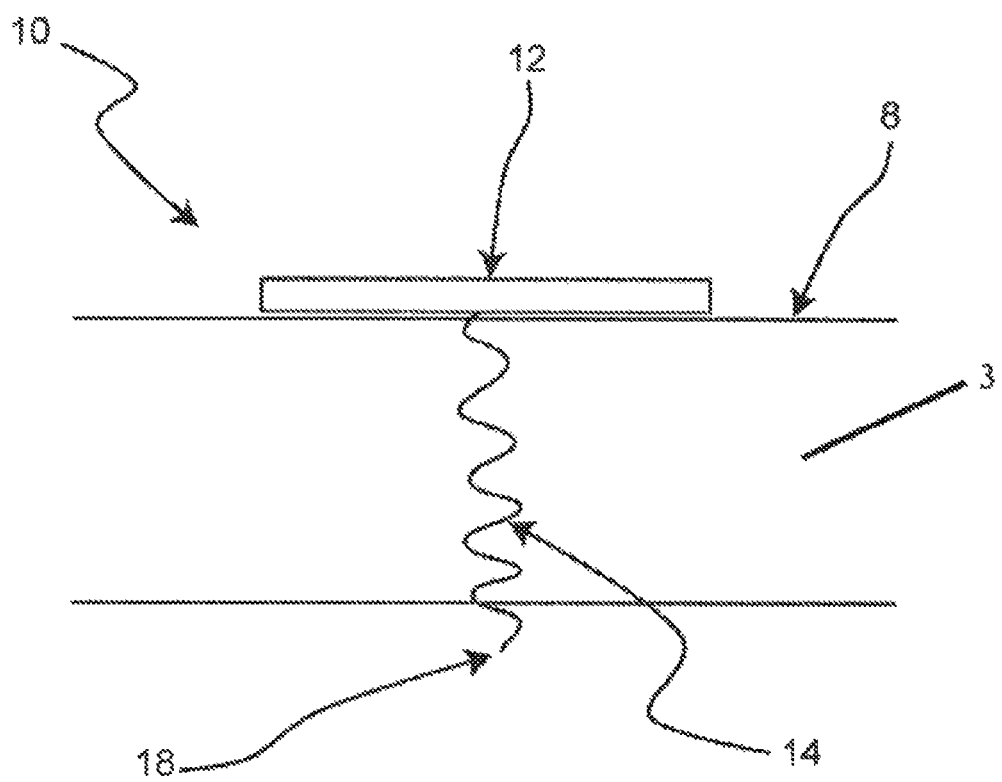
FIG. 7 is a schematic side view of an exemplary embodiment of an aspect of the present invention.

Referring to FIG. 7 and with particular but not exclusive reference to the third aspect of the present invention, a flexible substrate 3 is presented having a first side for contacting the biological barrier and a second side 8. A micro-penetrator arrangement 10 comprises a head 12 and projecting from the head towards the first side 4 is a projection 14. The projection extends from the head to a tip 18 wherein at least a portion of the projection 14 is curved intermediate the head 12 and the tip 18. As shown in the exemplary embodiment the projection is a repeating curved pattern. The curved pattern may be a linear projection twisted to form the final curved configuration. The cross-section of the projection 14 may be non-circular. The provision of a curved portion of the projection aids in transfer of a drug or biological material to the biological barrier 5.

In order to improve transfer of a drug or biological material through the biological barrier a further supplementary projection may be utilised. A supplementary projection may be wrapped around the projection 14 and/or may be intertwined with the projection. A supplementary projection may extend from the head.

Figure 8A:
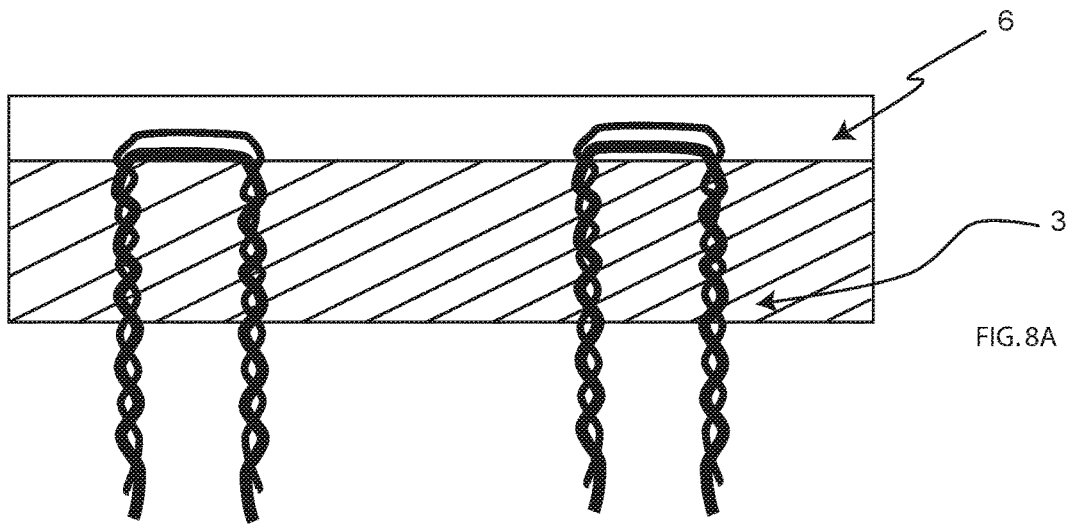
FIGS. 8a and 8b are further exemplary embodiments of an invention according to aspects of the present invention.
Figure 8B:
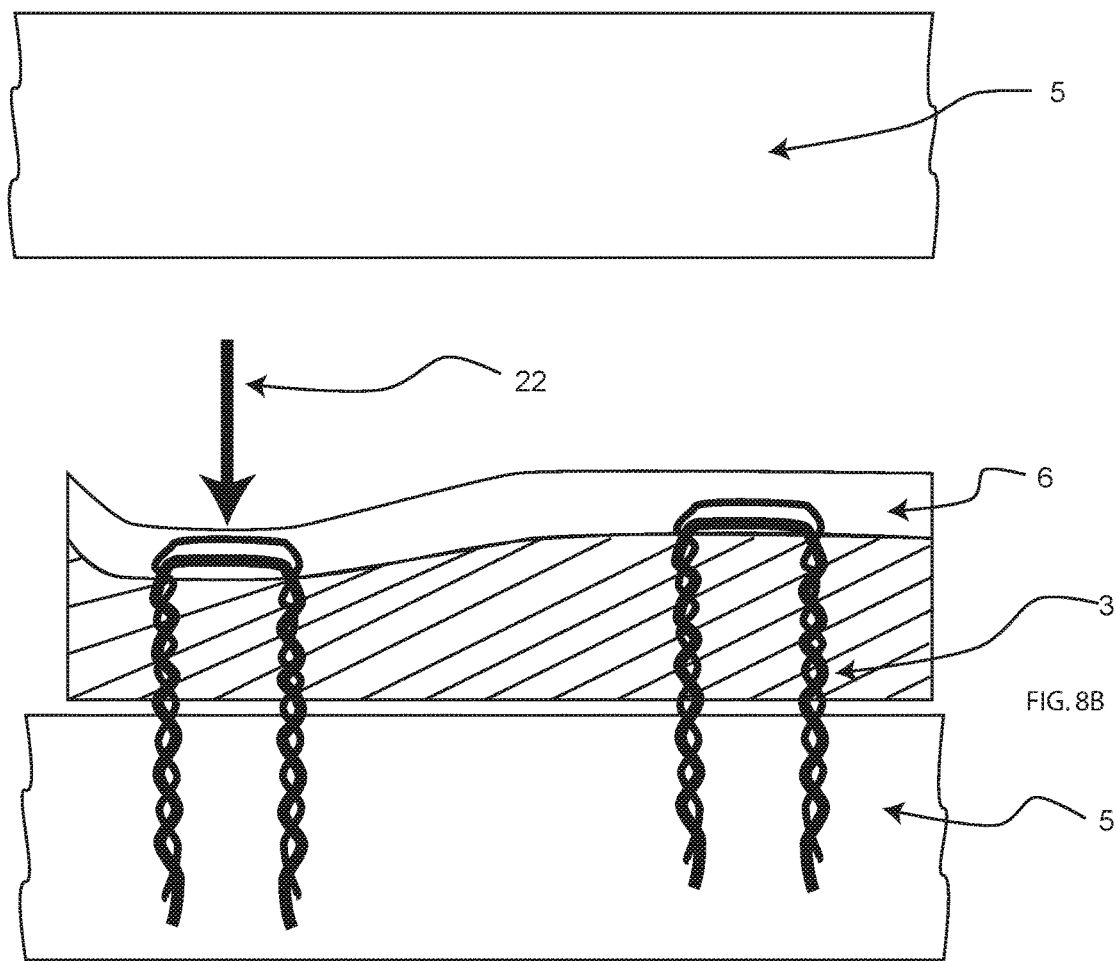

Referring to FIGS. 8a and 8b, a further embodiment is presented whereby the at least one projection 14 is at least partially curved. In this embodiment, a first and second micro-penetrator 10 may be provided whereby the respective projections are each intertwined.

Figure 9:
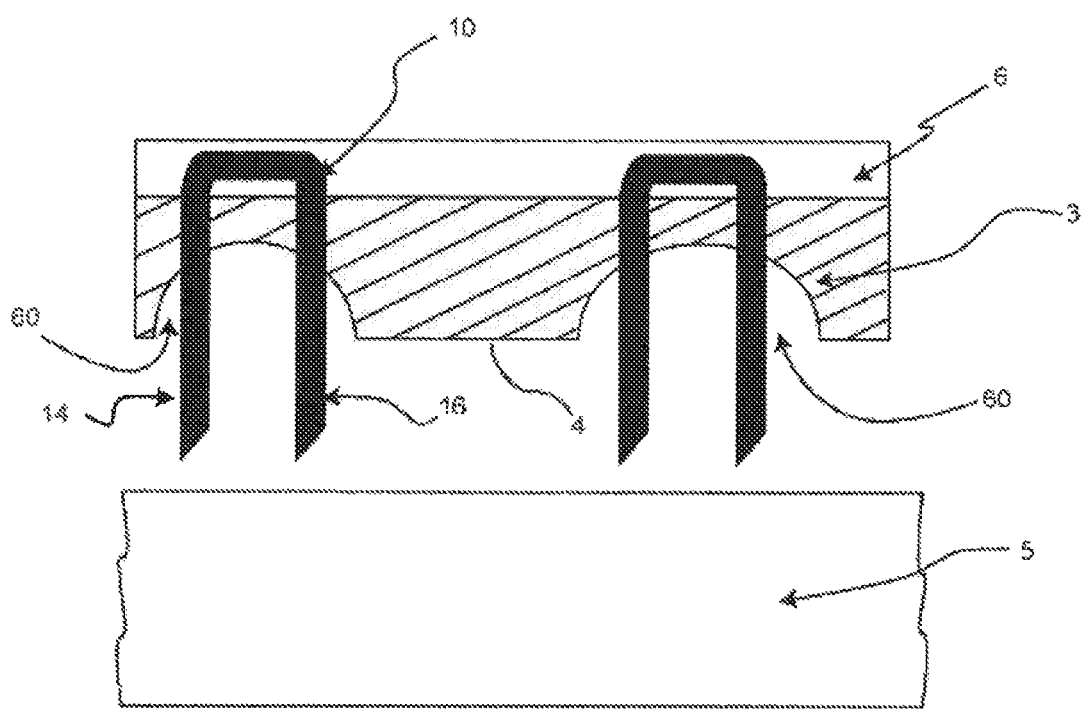
FIG. 9 is a further exemplary embodiment of the present invention.

Referring now to FIG. 9, another alternative embodiment according to aspects of the present invention is presented. Again an exemplary embodiment has been shown utilising supplementary layer 6 with the head 12 embedded therein. It is reiterated that supplementary layer 6 is not essential neither is the precise configuration of the micro-penetrator arrangement 10. In this embodiment, however, there are undulations 60 provided in the first side of the flexible substrate 3. The biological barrier contact surface is therefore sculpted and is beneficial in delivering liquids or solids applied to the contact surface of the device. This is particularly beneficial, for the purpose of getting an immune response, like an allergy diagnosis patch, or vaccine patch. The undulations and thus recesses formed are beneficially provided in the flexible substrate 3 and the one or more projections 14, 16 extend through the recess 60.

Figure 10:
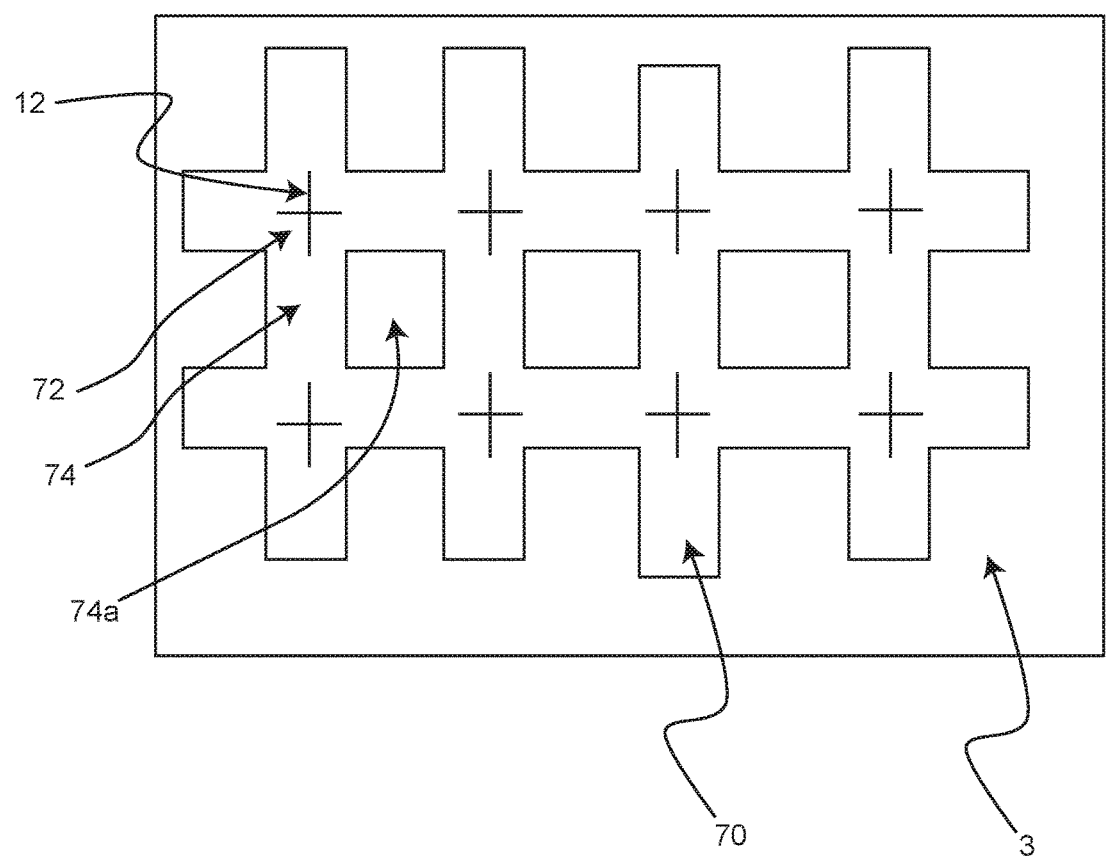
FIG. 10 is a schematic plan view of a further exemplary embodiment of an aspect of the present invention.

Referring to FIG. 10, there is a plan view of an exemplary embodiment of the present invention. In this plan view flexible substrate 3 is shown and layered in parallel with the flexible substrate 3 which effectively forms a first layer is a second layer 70. The second layer 70 is layered on top of the first layer. The layer 70 carries a plurality of projections projecting into the page as presented in FIG. 10. A variety of configurations of projection may be utilised including one or more projections having the form as described in any of the embodiments described herein. The projections may be integrally formed with the first layer 70 or as shown in FIG. 10 the head 12 is visible. As such the projections extending from the head 12 project through the first layer and through the second layer and subsequently into the biological barrier. A plurality of first zones 72 are provided from which a projection extends separated by a plurality of second zones 74. The second zones 74 also beneficially comprise a plurality of apertures 74a therein. It is beneficial that the first zones have a greater stiffness than the second zones as this ensures the projections do not deflect laterally upon insertion into a biological barrier and that as force is applied onto the first layer 70 the second zones can bend and flex such that treatment can be applied to the specific areas of the biological barrier as appropriate dependent upon the position of the applied force.

In another embodiment, the second zones may be provided configured to break or fracture upon applied force to enable accurate treatment of specific areas of the biological barrier without significantly impacting upon adjacent areas.

Referring to FIG. 11 in which presented a further embodiment of the present invention. In this embodiment the device is configured particularly for accommodating the anatomical profile of a fingertip. Accordingly, the second side 8 of the substrate 3 is beneficially concave. It is beneficial that the substrate material 3 is silicone rubber as such a material is readily conformable to the geometry of a fingertip. The opposing first side 4 is beneficially convex and in use a finger can be rolled across the skin to contact the projections 14, 16 with the skin to cause penetration. It is beneficial that the leading edge 8 is curved reflecting the leading edge of a fingertip whereas the trailing edge can be generally linear or curved depending upon particular requirements.

In any embodiment, the one or more projections of a micropenetrator arrangement may have notches, pockets, holes, serrations or undulations therein. Furthermore, they may be coated with other substances, such as another metal. In another embodiment, a projection may have a coating that terminates before reaching the distal end of the projection, such that the projection extends from the coating material. A coating may be provided for example to increase lubricity.

In any embodiment it will be appreciated that projections may be positioned sufficiently close to one another so that a material to be administered into the biological barrier may be carried and supported in the separation between the projections. The material may be a variety of materials as described elsewhere in the specification including for example a drug.

Aspects of the present invention have been described by example only and it will be appreciated to the skilled addressee that modifications and variations may be made without departing from the scope of protection afforded by the appended claims.

The invention claimed is:

1. A device for penetration of a biological barrier, the device comprising:
   a flexible substrate having a first side and a second opposing side;
   a plurality of micropenetrator arrangements each comprising a head, the head comprising a first elongate arm and a second elongate arm positioned in the form of a cross, a first and second projection, for penetrating a biological barrier, extending from the the first elongate arm, the first elongate arm spacing apart the first and second projections, a third and fourth projection extending from the second elongate arm for penetrating the biological barrier, the second elongate arm spacing apart the third and fourth projections, and the head abutting the second side of the flexible substrate;
   wherein a first and second adjacent micropenetrator arrangement are independent of each other; and
   the first, second, third and fourth projections extending through the second side of the flexible substrate towards the first side of the flexible substrate.

2. A device according to claim 1, wherein the flexible substrate comprises a different material to the micropenetrator arrangement.

3. A device according to claim 1, wherein the first, second, third and fourth projections project perpendicular to the head.

4. A device according to claim 3, wherein the first, second, third and fourth projections project from the first side.

5. A device according to claim 1, further comprising a supplementary layer disposed on the second side of the flexible substrate, the head being encapsulated by the supplementary layer.

6. A device according to claim 1, wherein the first elongate arm and the first and second projections are formed of a single elongate bent element.

7. A device according to claim 1, wherein the head and first and second projections are formed of a metallic material.

8. A device according to claim 1, wherein the first and second elongate arms comprise an overlap zone of overlapping first and second elongate arms, and the first and second elongate arms are joined at the overlap zone, and the first and second elongate arms are mutually perpendicular.

9. A device according to claim 1, wherein the first and second elongate arms of the first micropenetrator arrangement are parallel to the respective first and second elongate arms of the adjacent second micropenetrator arrangement.

10. A device according to claim 1, wherein the substrate comprises a leading edge and a trailing edge, and the leading edge is curved to generally conform to the leading edge of a finger.

11. A device according to claim 1, wherein at least a portion of the first, second, third and/or fourth projection comprise a curved portion.

12. A device according to claim 11, wherein the curved portion comprises a plurality of repeating curved portions.

13. A device according to claim 1, further comprising a supplementary projection arranged such that at least one of the first, second, third and/or fourth projection are in communication with the supplementary projection for penetration of a biological barrier.

14. A device according to claim 13, wherein the supplementary projection is intertwined with at least one of the first, second, third and/or fourth projection.

15. A device according to claim 1, wherein the first side of the flexible substrate carries a drug and/or biologically active material therein.

* * * * *